United States Patent [19]

O'Harra

[11] Patent Number: 4,935,635

[45] Date of Patent: Jun. 19, 1990

[54] SYSTEM FOR MEASURING OBJECTS IN THREE DIMENSIONS

[76] Inventor: Dale G. O'Harra, 2230 Semeria Ave., Belmont, Calif. 94002

[21] Appl. No.: 282,209

[22] Filed: Dec. 9, 1988

[51] Int. Cl.[5] ............................................. G01N 21/86
[52] U.S. Cl. .................................... 250/560; 250/561; 356/376
[58] Field of Search .................... 250/560, 561; 356/1, 356/4, 376, 381

[56] References Cited

U.S. PATENT DOCUMENTS

| | | | |
|---|---|---|---|
| 4,089,608 | 5/1978 | Hoadley | 356/376 |
| 4,743,771 | 5/1988 | Sacks et al. | 250/560 |
| 4,792,698 | 12/1988 | Pryor | 250/561 |

Primary Examiner—David C. Nelms
Attorney, Agent, or Firm—Thomas M. Frieburger

[57] ABSTRACT

A three-dimensional measuring system particularly for dental and other space-limited uses has a laser diode projecting a triangulating beam at a surface to be mapped, with the beam scanned repeatedly across the surface. Photodetectors detect the position of the beam as reflected from the mapped surface, giving by triangulation Z-axis or depth information. Correlation of a particular point with the position of the scanner along the scan line gives Y-axis information, or information in a width direction. The scanner and diode are mounted on a slide or platform device which moves perpendicularly to the Y axis in the direction in and out of the mouth, driven by a stepper motor, and the monitored position of the stepper motor is coordinated with the other information on each spot to yield X-axis information.

21 Claims, 7 Drawing Sheets

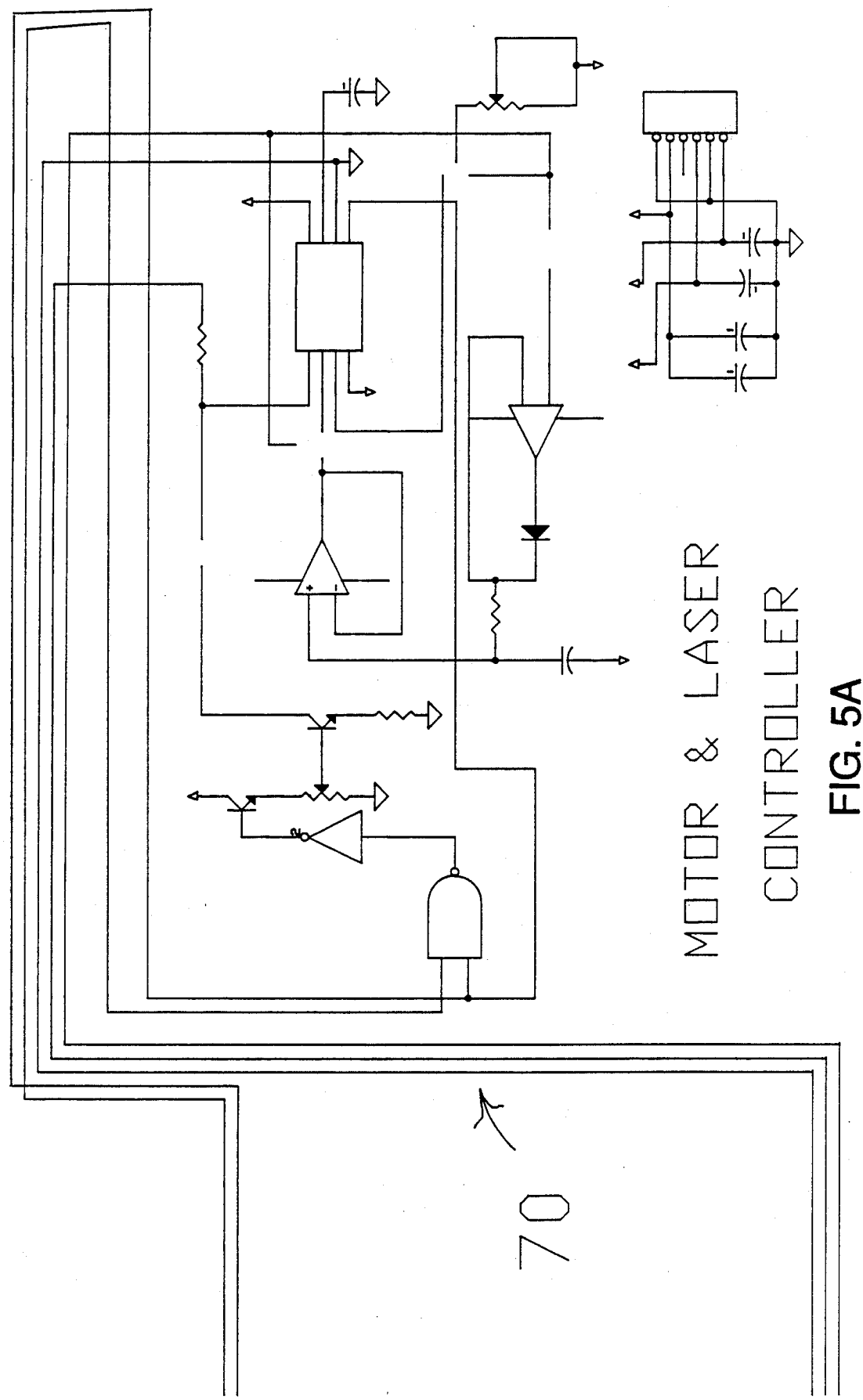

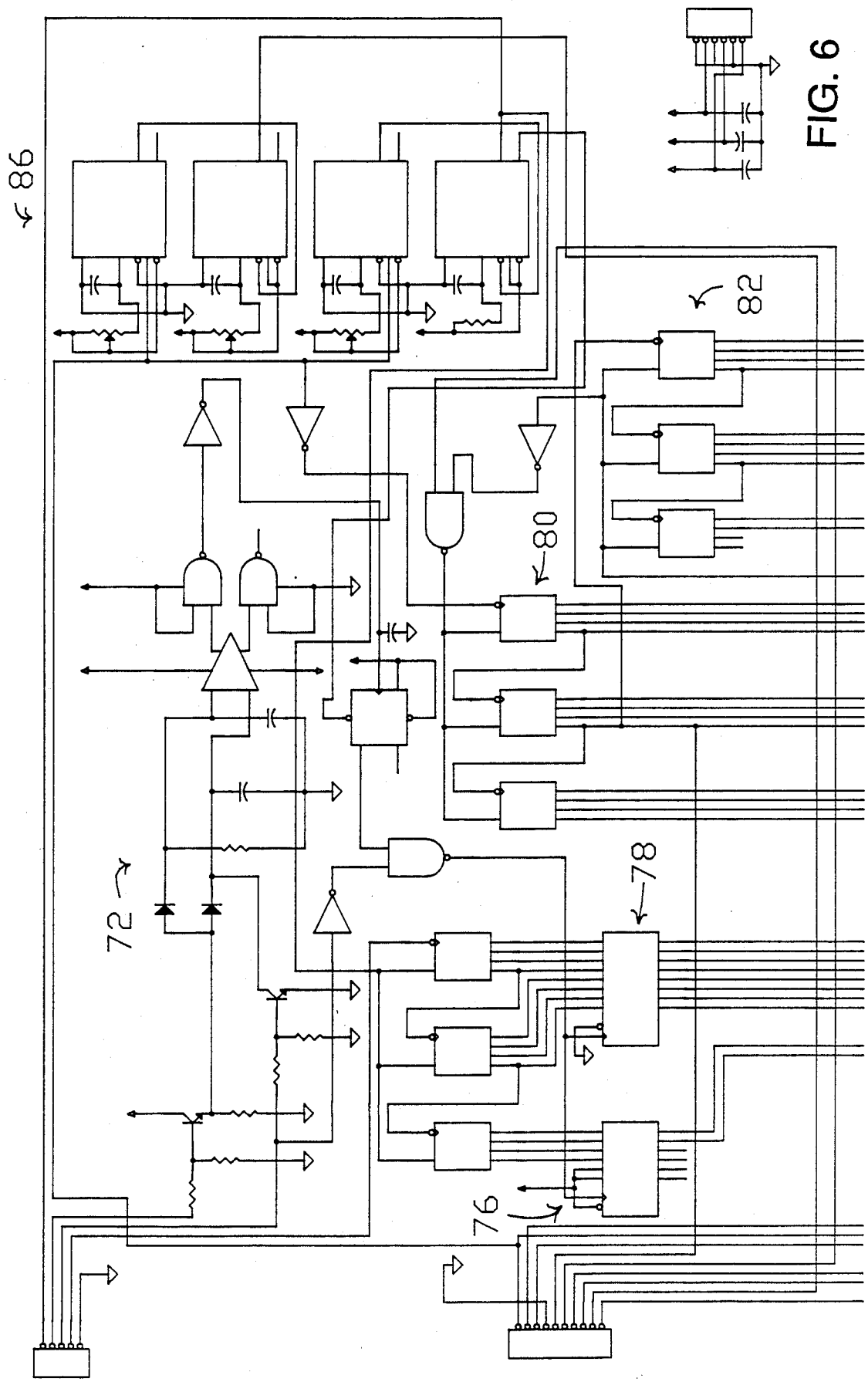

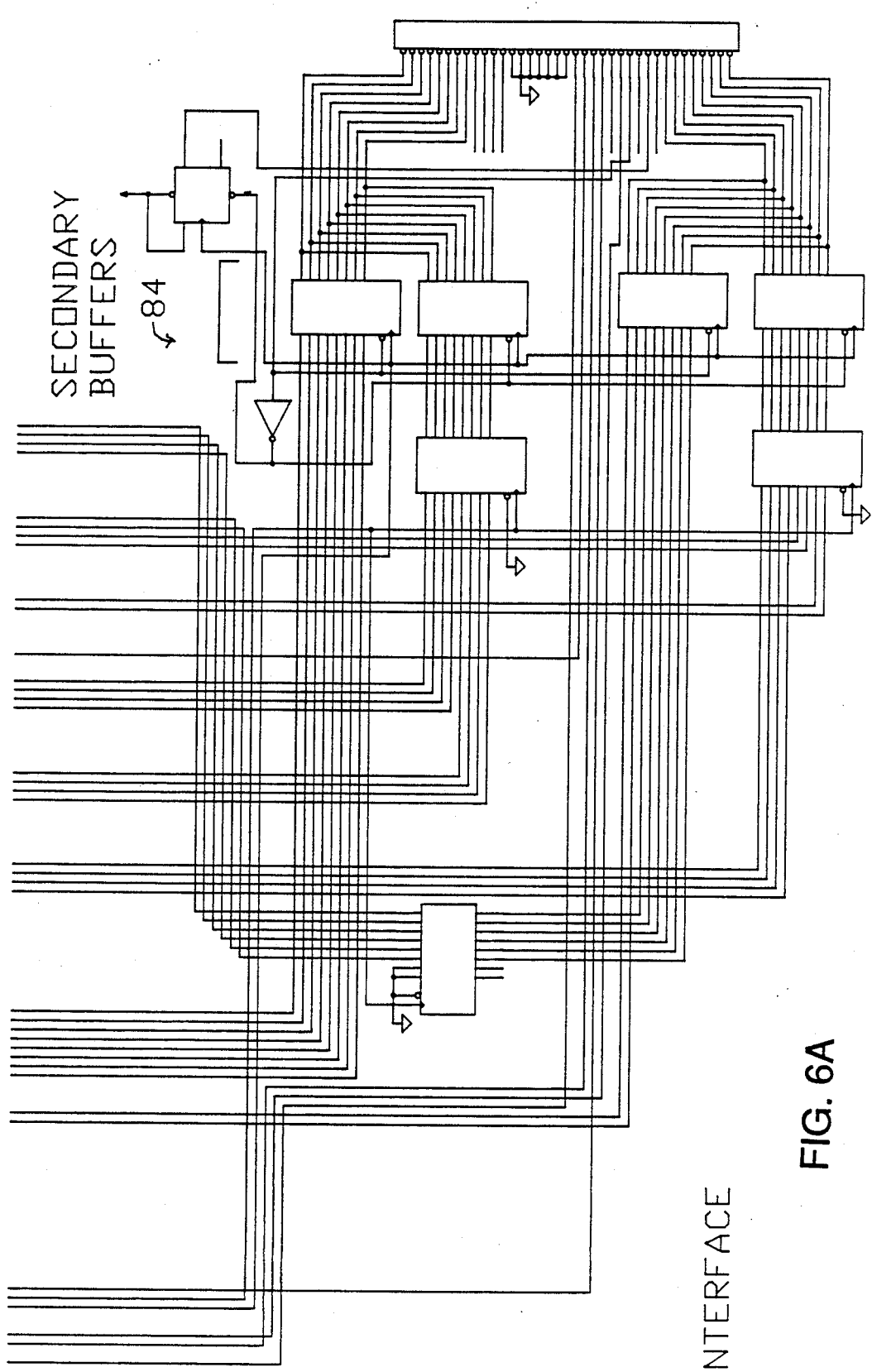

SYSTEM FOR MEASURING OBJECTS IN THREE DIMENSIONS

BACKGROUND OF THE INVENTION

The invention relates generally to sensing and measuring equipment and methods, and particularly to a system for automatically scanning, mapping and reproducing the dimensions of three dimensional objects. In one specific aspect, the invention has application to dentistry, for scanning, mapping, and storing the three-dimensional topography of teeth, for dental restorations.

Various systems and methods have been suggested for three dimensional mapping or surface measuring of objects. Among these has been a system intended for dental applications and comprising a triangulating device with two cameras looking at each survey point from different angles. This system was very costly, and yet had a resolution of only about 200 microns.

Other systems in the general field of three dimensional mapping or topography measuring and recording have also made use of the conventional triangulation scheme wherein either two cameras have been aimed at a spot from different angles, thereby giving a relief measurement or distance from the cameras, or a narrow light beam has been projected at an area from one angle and a camera has recorded from another angle the position of the light beam, similarly giving the relief distance measurement. In some of these prior systems galvo scanners have been employed. The galvo scanners have required too much space to enable miniaturization as achieved by the present invention and as necessary for dental applications. Further, they tend to require a great number of calculations and thus a powerful computer.

None of the prior systems has been as simple, efficient, rugged and reliable, capable of relatively high precision, while also being small and compact to the extent of easily fitting as a probe into a dental patient's mouth, as is the apparatus and system of the present invention described below.

SUMMARY OF THE INVENTION

In accordance with the present invention, a fine precision, miniaturized three-dimensional topographical mapping system easily fits in a dental patient's mouth and uses triangulation and the recording of position on three orthogonal axes in a unique and advantageous manner. The system of the invention includes a narrow probe (preferably 16 mm or less in diameter or width) with a sliding platform member driven by and precisely controlled by a stepper motor which may use a screw drive to move the sliding member, on an X axis. In the dental context, the X axis comprises movement in a direction into and out of the mouth, i.e. parallel to the rows of teeth. The position of the sliding platform member is precisely known via the pulses fed to the stepper motor, so that when a measurement is taken, the X-axis position of the sliding member is recorded relative to a reference or zero position.

A Z-axis measurement is made using triangulation involving a laser beam, on the one hand, and a type of camera on the other, the two being separated and angled so as to measure by triangulation. The camera may comprise a photodetector strip, preferably an array of photodetectors, permitting compactness and very small scale arrangement of components.

Z-axis information is obtained by the triangulation, i.e. the depth or relief distance of the feature from the camera or the platform, or in a preferred embodiment, from a cylindrical lens which focuses a returning image on the photodiode array.

At the time a spot is measured by the laser beam/camera combination, the position of the laser beam in a reciprocating or rastering type scan or sweep is precisely recorded, giving Y-axis information.

By the method, apparatus and system of the invention, and particularly in specific embodiments, a very high degree of miniaturization is achieved, while still permitting reliability and precision at least adequate for obtaining mapping measurements for adequate reproduction of the surfaces of teeth. In one preferred embodiment resolution of 50 microns is achieved, with an instrument having width or diameter dimensions not exceeding 16 mm. The instrument is rugged and capable of sterilization.

In the specialized dental applications of the invention, a special dental probe instrument preferably scans three teeth at a time, digitizing points scanned in X, Y and Z coordinates to an accuracy at least as good as 50 microns. The probe can form a part of a complete dental system which includes an occlusion machine, displays, and electronic support systems, as well as a device for producing restorative teeth or portions of teeth. The dental probe device in a preferred embodiment is inexpensive to manufacture and very easily used and maintained.

The system of the invention is capable of very rapid setup procedures, data acquisition and data processing. It is generally necessary to do more than one view of the teeth being digitized, e.g. three views. The three views may be a top (or bottom) view and both side views. In a computer the three images can be put together in a composite three dimensional view.

Data acquisition can take place at the dental office, with the dental laboratory taking care of substantially all other functions. The dental office may have limited CAD capability for the dentist, adequate to determine if a valid three dimensional image has been obtained, thus insuring a usable digitized impression for the laboratory.

The laboratory system can include CAM software, allowing the dental technician to view the teeth in many different views, and also to splice the views to form the composite three-dimensional picture. Editing capability is required, to edit the files to remove any bad data or to change contours as desired. The output of this CAM software can be put into a multi-axis milling machine which recreates the desired prosthesis.

The data can be transmitted from the dental office to the laboratory in a number of different ways. Generally, it can be physically transported on a floppy disc, but it could also be transmitted by a fiber optic or fast LAN data link or other high bandwidth communication system.

While data is being gathered in the dental office, it is being placed in the image memory and can simultaneously be displayed on a monitor, such as an EGA quality color monitor, in a variety of possible formats. Once a scan is complete, the image can remain in the image memory until replaced by another scan or until a new image is downloaded from a floppy or hard disc. The image can subsequently be displayed in a desired format, converted to a CAD or other type file, saved, or discarded.

Resolution of the system of the invention is at least as good as 50 microns in X, Y and Z directions. With the embodiment described below, resolution is approximately 30 microns on the Z axis, and 50 microns on the X axis. Y axis resolvability is variable along the axis but is on the same order as resolution on the other axes.

Actual system accuracy can improve over the above figures through the use of spline fits in the CAM software, as the three-dimensional spatial frequency of the tooth is very low. The tooth generally comprises smoothly connected surfaces with only a few directional changes per unit length of the subject surfaces in any dimension.

The system of the invention uses the principle of three-dimensional triangulation. The two lines triangulated are a projected collimated light beam, preferably a laser beam generated by an infrared diode laser, and a line from the impinging beam on the target to the imaging lens of a detection system.

In this system, the point of light emission is well known. The beam is being directed in two dimensions by the scanning system. The X direction movement is generated by a stepper motor moving the system along the tooth. The Y direction movement is generated by a rotating polygonal reflector (or a holographic scaner) which scans the beam across the tooth. In this case, the 12 facets of the reflector result in 12 scans per revolution of the reflector. The motor rotating the polygon has an encoder which sends positional data to the phase locked motor control system. As this is a phase locked system, encoder data can be synchronized to a much higher frequency counter, hence the encoder counts can be broken into any number of subcounts to obtain accurate position information of the rotating polygon. The dental application in a preferred embodiment uses 256 points for each of the 12 facets of the polygon.

The Z direction (height) is obtained from the location of the spot of light generated by the laser hitting the tooth, as seen by the imaged array of photodetectors.

In order to provide synchronization of the probe's movements, and to know exactly where the start of an image is, the reflected laser beam coming from the polygon not only scans the object but also scans across a photodetector before scanning the object. This photodetector's output is used to indicate start of scan, thus synchronizing all of the facets of the rotating polygon and relaxing substantially the requirement for face to face variation of the polygon. This translates directly to lower manufacturing costs.

The output of the laser is focused using an aspheric, AR coated plastic molded lens which focuses the beam on the tooth. The path length is chosen to be long to minimize spot size variation over the field of depth required.

The overall optic path is then from the laser, through the focusing lens, off the rotating polygonal reflector, and on to the tooth. The impinging light (focused point) is observed by a cylindrical lens (for removing all but Z axis dimensionality) which images the spot onto a linear charge-coupled photodiode array for determining height. The actual value of height is obtained by determining the location where the most light falls on the array (through an electronic peak detection scheme) and a trigonometric equation using the computer's floating point numeric coprocessor.

This configuration results in a very simple mathematical coordinate system thus minimizing the amount of computations required. The X direction is simply the position of the stepper (no math required). The Y direction is simply the position of the rotate and a trig identity. The Z direction is simply the position of the spot on the sensor and a trig identity.

The data is gathered in raw form, presented and stored in the image memory. It can then be converted to real world coordinates at any time later using the numeric coprocessor.

Mechanical movement is controlled to the required accuracy through the use of precision linear bearings and various spring preloads to eliminate any play or wobble in the motor rotate system, the motor 9:1 gearbox, or the stepper lead screw system.

The diode laser can be easily modulated at frequencies to 1 gigacycle and can be actually strobed to produce a freeze frame effect when digitizing points. This results in less blurring of the scanned beam, hence better positional accuracy.

In order to get the data into the computer at the required data rate, a multiplexed 16 bit bus can be used from the probe electronic system to the computer to split the 32 bit probe system bus using split cycle timing.

All X, Y, and Z coordinates are formed in a four-byte double word. Thirty-two bytes is enough to represent all raw coordinates of an interrogated point on the tooth (pixel).

A method for rapidly calibrating the probe for retrieving actual measurements from scanned data has been developed in accordance with the invention. The calibration compensates for variations in height from the collection lens caused by scanning through an arcuate path (which tends to cause remote edge-of-scan points to read farther away than central points in the scan). It also compensates for non-linear correspondence of photodiode array readings to heights caused by trigonometric considerations of the angled scan. This method is faster than a pure mathematical conversion of each data point to other data point using a math coprocessor. The method consists of scanning a known calibration test object, processing the data and storing in a special calibration file. The data from this file can later be used to normalize the raw data from any scanned object. This method avoids the need for any trigonometric calculations or mathematical lookup tables and is thus very rapid and does not require the use of mathematic coprocessors. An added benefit is that each manufactured probe is calibrated using this technique individually and thus any errors stemming from geometric probe-to-probe variations are compensated for. A preferred calibration test surface is an inclined plane whose correct height points are precisely known.

Accordingly, it is among the objects of the present invention to provide a three-dimensional mapping apparatus which achieves a high degree of accuracy, adequate for dental applications, miniaturization at least adequate for convenient use in dental applications, and simplicity and reliability in operation, in an instrument of superior construction as compared to prior instruments and systems. These and other objects, advantages and features of the invention will be apparent from the following description of a preferred embodiment, considered along with the accompanying drawings.

DESCRIPTION OF THE DRAWINGS

In FIG. 1 the device is shown as it might be used in a dental application, to measure and map teeth in a patient's mouth.

FIG. 4, 5, 6 and 7 are a series of schematic circuit diagrams relating to the system of the invention.

DESCRIPTION OF PREFERRED EMBODIMENTS

Figure 1:
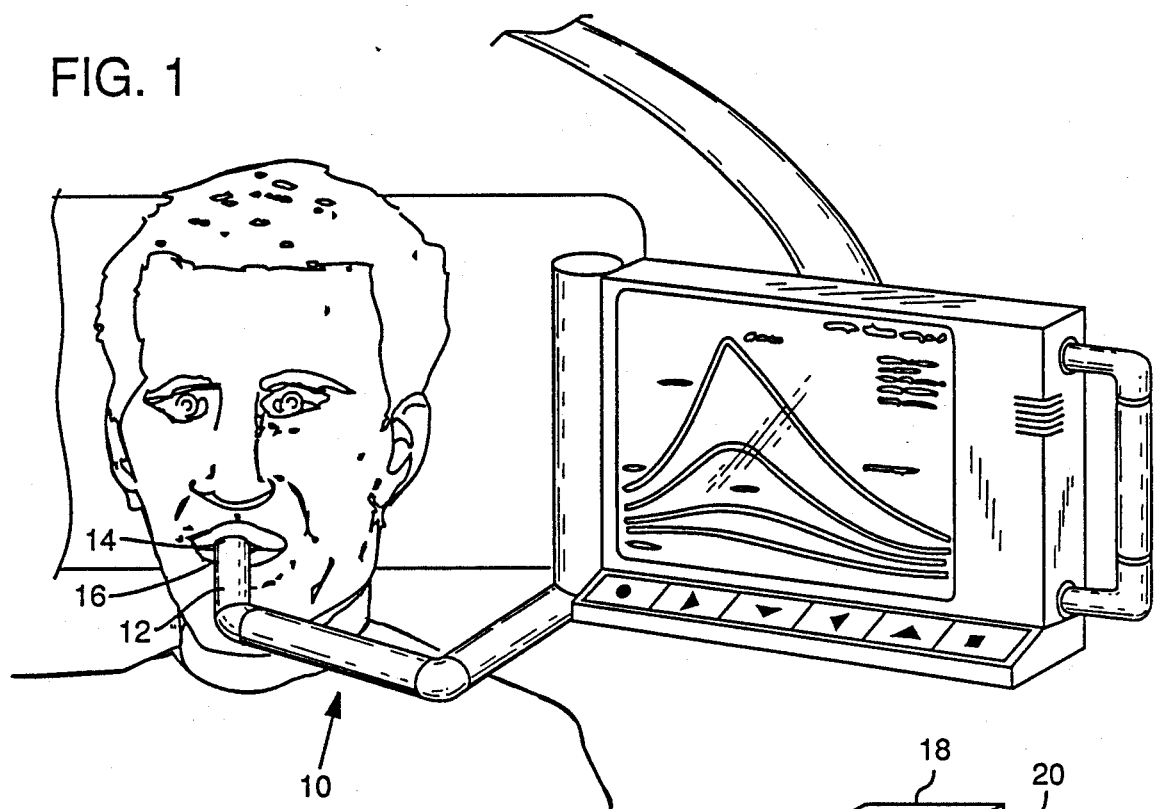
FIG. 1 is a perspective view showing one embodiment of a precision three-dimensional mapping device in accordance with the principles of the invention.

In the drawings, FIG. 1 shows a precision three-dimensional mapping device identified by the reference numeral 10, of very compact configuration and small size, positioned in a dental patient's mouth for recording three-dimensional information or topography of the patient's teeth. The mapping device 10 has an outer housing 12 and a probe-like end 14 which extends into the mouth. At one side of the probe end 14, capable of orientation in any direction, is a beam scan window 16 through which a collimated or focused light beam such as a laser beam is projected and scanned to obtain topographical information by triangulation, as further explained below.

Figure 2:
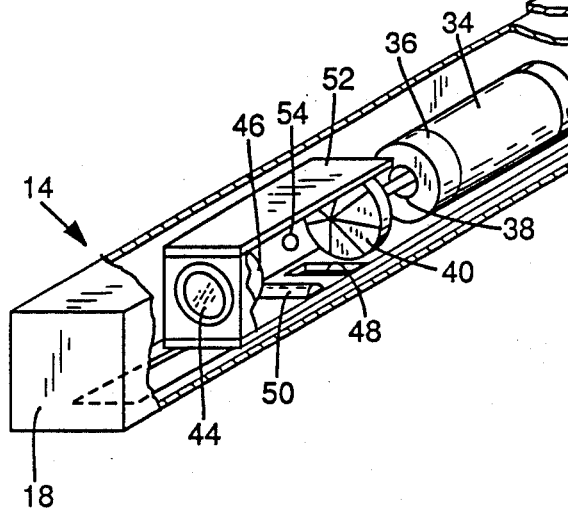
FIG. 2 is a perspective view with portions of an outer casing of the device removed, showing the construction and operating principles in accordance with a preferred embodiment of the invention.

FIG. 2 shows the topographical scanner or three-dimensional mapping device 10 in perspective, with portions cut away to show components. An outer housing 18 of the device extends the length of the probe but is broken away in FIG. 2. At a base end 20 of the unit a motor 22 is enclosed, which may be a linear stepper motor in accordance with the invention. The motor 22 drives a threaded screw shaft 24 which engages with a female threaded component 26 which is at the right end (as viewed in FIG. 2) of a movable slide platform or sled 28 which moves in the X direction and bears the scanning and height sensing components, as outlined above. The X axis movement, in use of the device, is generally along a row of teeth in the patient's mouth.

The slide platform or sled 28 is mounted on a precision roller bearing linear slide 30, which acts between the outer housing and the sled. The precision bearings can be preloaded, but preferably they are of the type that are accurate in position to within a few microns. However, there preferably is included some form of preload for the screw/thread connection and to prevent any X-axis movement inside the motor bearings This can comprise a preload spring 32 as shown in FIG. 32, which can be either a compression spring or tension spring.

The sled 28 supports the scanning system and the height measuring system of the probe device. The scanning system includes a scan motor 34, the output of which is geared down by a gear box 36. An upward shaft 38 from the gear box has secured to it a rotating polygonal reflector 40 or other scanning device which may have, for example, nine to twelve mirror facets.

A motor shaft encoder indicated at 42 is used in a phase locked loop to precisely control the speed of the scanner motor 34. The phase locked loop, as will be explained further below with respect to the circuit diagrams, senses overspeeding or underspeeding of the motor and makes corrections so that the speed is kept within a preselected tolerance.

Forward of the scan motor and polygon reflector is a laser source, preferably a laser diode 44 which outputs a beam which is focused by a laser focusing lens 46. The beam, then converging, is reflected off the facets of the polygonal mirror 40 and is angled downwardly (as seen in FIG. 2) through an exit slit 48 in the sled and then through an exit window 16 in the outer housing to impinge on the teeth being surveyed. The impinging beam spot is viewed through the same scan window 16 (not shown in FIG. 2) and the returning light from the reflection off the teeth is imaged through a cylindrical lens 50 onto a charged coupled photodiode array 52, the back side of which is seen in FIG. 2. The position of the returning imaged beam spot along the length of the photodiode array indicates the height or Z-axis distance of the particular point being surveyed away from the cylindrical lens 50. For example, the total length of the photodiode array might be about 15 to 25 millimeters, with 1000 pixels on 15 to 25 micron centers. The cylindrical lens 50 removes from the returning light spot all directional components except for the height information desired—i.e., the returning focused spot of light is in the form of a narrow transverse line, whose position is sensed along a perpendicular line of photodiode pixels, i.e. in an array following a longitudinal line with respect to the length of the probe.

The use of a charge coupled photodiode array is preferred for several important reasons. The diode array is more sensitive to light than position sensitive lateral effect photodiodes, resulting in operation at reduced beam intensity levels or greater distance; and in the preferred type of array, the position of each sensing pixel is geometrically fixed, thus eliminating positional errors due to environmental effects such as temperature.

A photodetector 54 is shown adjacent to the beam scan exit slit 48, in the path of the beam exiting from the scanner 40. This photodetector is used to sense the start of a scan line of the beam. Because of inevitable slight variations from facet to facet of the rotating polygonal mirror 40, the precise position and sweep of the generated scan lines will vary. However, the photodetector 54 indicates a start position of each scan, which will be within the mirror of each mirror facet of the polygonal reflector 40. The start of scan photodetector 54 thus overcomes any problems which would be caused by variation in the angle between adjacent mirror facets, and it also removes from consideration variations in the "rolloff" area between facets, at the break in angle. The photodetector 54 is connected to the electronic circuitry (explained below) and is used to reset counters for start of scan, for each facet.

There preferably is also a preload spring of an appropriate form bearing against the output shaft 38 from the motor gear box 38, to preload the position of the rotating polygonal reflector and avoid any longitudinal or lateral wobble in the position of the reflector.

Thus, it can be seen that X, Y and Z positional information for each surveyed point or spot on the object being surveyed is determinable from the components shown in FIG. 2. The stepper motor position or X-axis position is known through the driving circuitry, since each pulse delivered to the stepper motor 22 causes rotation and X-axis movement by a certain known amount. Y-axis information is determined by the precise position of the laser beam in each scan line, with each facet of the multi-faceted scanning element 40. As mentioned above, the start of scan is sensed by the light beam striking the start of scan photodetector 54 as it is reflected off the mirror facet, and this is used to start a counter which will correlate the Y-axis position with the known speed of rotation of the polygonal reflector. The phase locked scan motor 34 is dependable as to its precise rotating speed within each scan, and the counter is reset to zero each time the photodetector senses the beginning of the scan.

Z-axis information is obtained by triangulation, i.e. the position on the charged coupled photodiode array 52 on which the reflected impinges.

Figure 3:
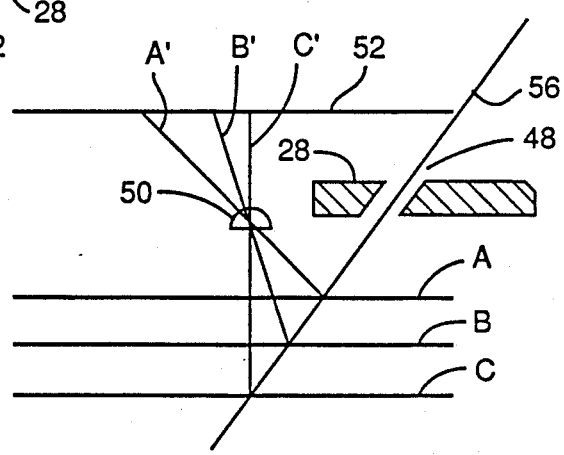
FIG. 3 is a detailed view illustrating a triangulation principle and a photodetector camera for obtaining information along two orthogonal axes for the mapping function.

FIG. 3 shows the basic principle of the Z-axis triangulation height determination, as used by the instrument of the invention. The beam reflected off the rotating polygonal mirror facet is shown at 56, passing through the beam exit slit 48. The beam 56 is passed out through the slit at an angle, which may be at about 30 to 45 degrees from the vertical, in order to project forward somewhat, so that small objects or teeth can be sensed which are near the end of the probe, toward the back of the mouth. The beam 48, which is sweeping in the Y-axis direction (into and out of the paper as seen in FIG. 3) strikes surfaces of the teeth at different depths.

FIG. 3 shows schematically three different depths A, B and C, at which the beam 56 might impinge. If the beam strikes the object or tooth at level A, its light, which is scattered with a Gaussian distribution, will pass through the cylindrical lens 50 and strike the photodetector array 52 at a point A'. If the beam strikes the object or tooth at level B which is at a greater distance from the cylindrical lens 50 as shown in the drawing, its light will pass through the cylindrical lens to strike the photodetector array at a point B'. If the beam 56 strikes the tooth at level C as shown in FIG. 3, its reflected light will strike the array at a point C'. It can be seen that the difference in position along the photodiode array 52 is essentially proportional to the difference in depth sensed. This is not a linear function, but a geometric function—however, within a narrow range with which the system is concerned in surveying small objects with relatively minor surface relief variations such as teeth, the differences in position along the array are essentially linear. Even if objects with greater relief are to be sensed, the geometric variation can be accommodated in the software associated with the system, in a variety of ways. A preferred method is to perform a calibration on each manufactured probe, which compensates for these non-linear readings and also for probe-to-probe physical variations and for variations in the height readings caused by scanning through an arcuate path (edge-of-scan points tend to read farther away than central points, for a given actual height). The method involves a simple calibration by scanning an object of known height at all points, such as an inclined plane. The probe is advanced over the plane with the plane inclined symmetrically along the X axis. The read data is subtracted from the actual known dimension data, and the resulting error value is used to correct all readings in the computer.

The scanned beam 56 can be a collimated beam or a focused beam which is converging as it approaches the target, as discussed above. A focused, converging beam has the advantage that it diverges as its distance from the source becomes greater, thus reducing potential eye hazard. The degree of convergence, or effective focal length of the system, is such that a long beam waist is produced, giving a greater depth of field for purposes of surveying the teeth at different relief heights.

Figure 4:
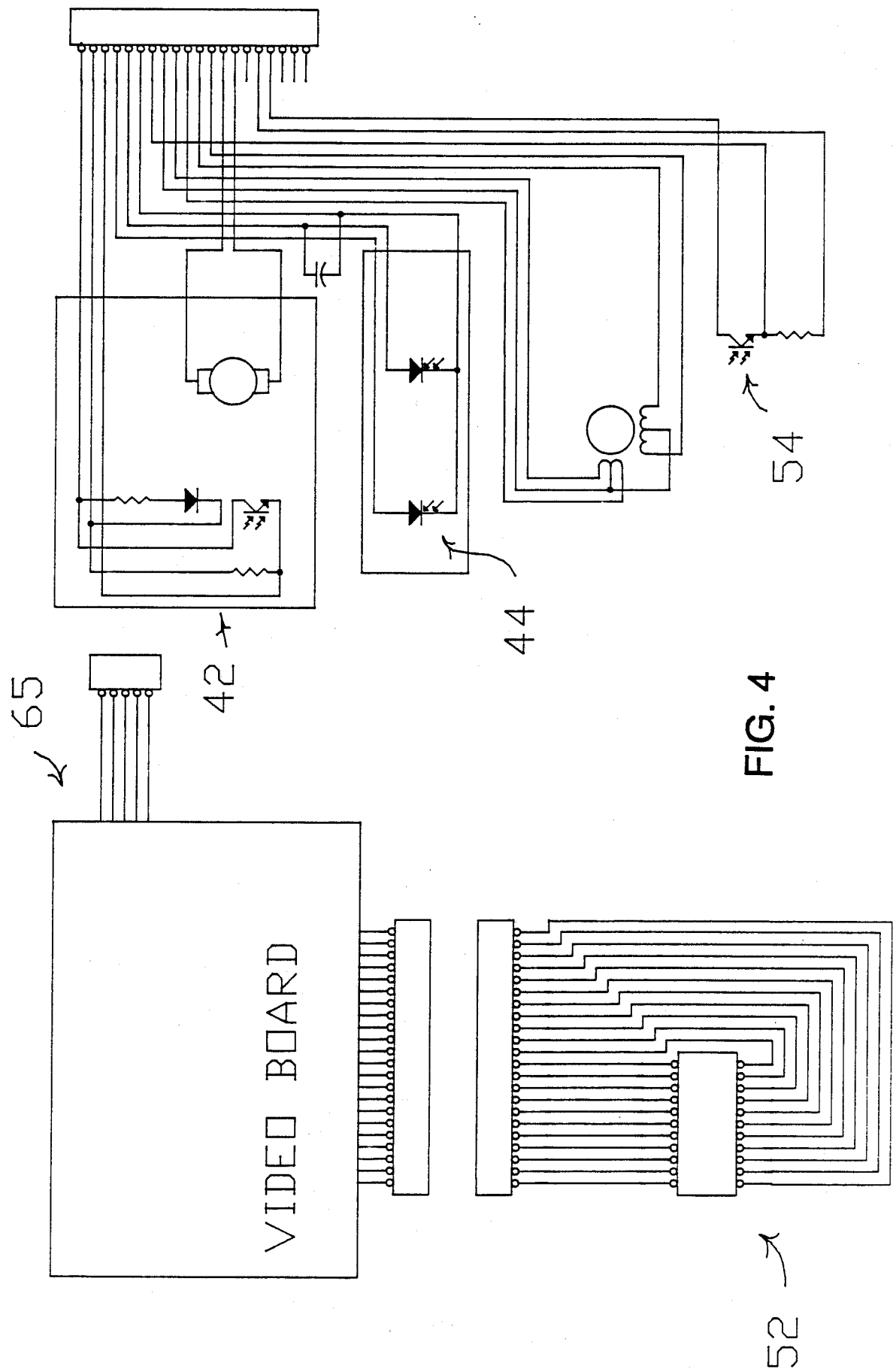
Figure 5:
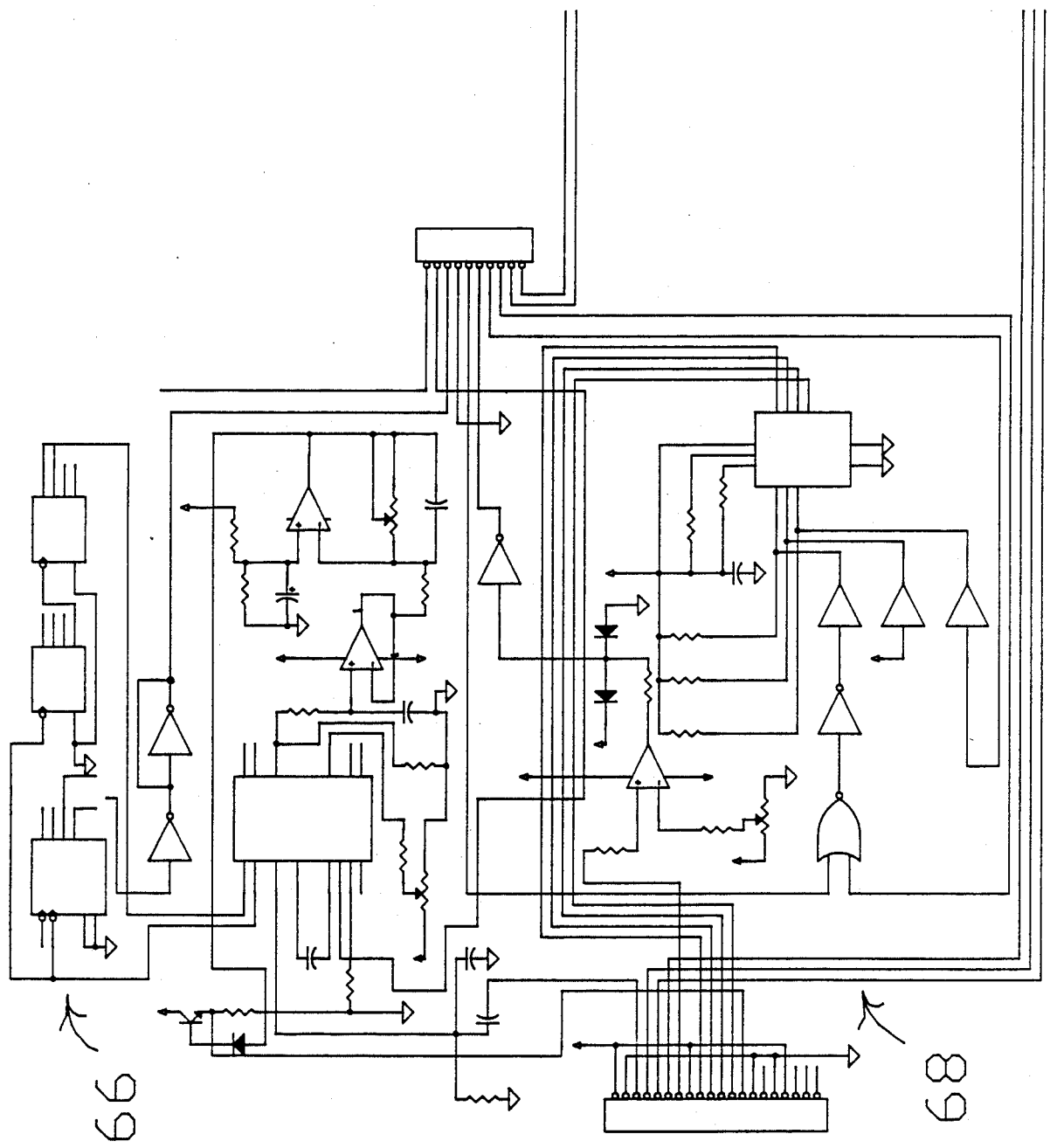

FIGS. 4, 5/5A, 6/6A and 7 are related circuit diagrams showing aspects of the system of the invention.

FIG. 4 shows the actual components from an electrical standpoint that reside within the probe housing itself. The first component is the charge coupled photodiode detector 52, and its connections are brought directly out of the probe. The second part of the probe electronics consists of the Y-axis motor 34; it is preferably a simple DC motor which is used in a servo loop to control the speed accurately. It has attached to it a built-in encoder 42, the output of which is used to measure the speed of the motor. The third electronic component in the probe housing is the laser light source 44 which consists of a laser diode assembly; the laser diode assembly has its own photodiode built in to measure the laser light output, and is used to control the current going to the laser to keep the light output constant over the life of the laser diode.

The fourth item in the probe is the X-axis stepper motor 22; this is the motor that drives the sled longitudinally down the row of teeth. A fifth item in the probe is the photodetector 54 used for start of scan acquisition. These are the components that comprise FIG. 4 and are interfaced to the rest of the electronics for the probe.

FIG. 4 indicates a video board 65 which is to be connected to the charge coupled photodiode array 52. This can be a commercially available video board. However, the, video board can be incorporated in the circuitry of FIG. 5/5A if desired.

FIG. 5/5A consists of three major circuits: the first circuit is the phase lock loop controller 66 for the Y-axis motor for scanning the laser beam. It is very important that this laser beam motor go at a very constant speed; thus, to control that speed, a reference frequency which is generated within the phase lock loop circuit is compared to the frequency of pulses coming from the motor encoder. If the motor is running too slowly, the voltage is increased, thereby increasing the motor speed; and the speed is decreased if the motor is running too fast. This is a standard phase lock loop technique for controlling motor speed, and results in very stable speeds.

The reference oscillator in the phase lock loop circuit is also used as the master oscillator to control the speed of everything in the probe; as a result, the stepper motor steps longitudinally in the X-axis, and the laser is strobed in synchronization with the rotating motor's speed. A counter circuit comprising U28 and U12 is used to generate pulses corresponding to the position of the laser beam as it is scanned in the Y-axis. These pulses are phase locked to the rotate speed of the motor, so that accurate representation of where the laser spot is in the Y-axis dimension is generated for the computer. The counter in the illustrated embodiment is configured so that 256 separate pulses are generated per each scan of the beam, or 256 times the number of scan facets per revolution of the motor.

A second portion of FIG. 5A, is the circuitry comprising U-20, U-22, U-31 and U-21, shown as 68. This circuitry is a standard stepper motor controller, and takes signals from other portions of the circuitry to generate pulses to move the X-axis stepper motor in synchronization with the rest of the system.

A third major portion of FIG. 5A is the laser controller 70. This system consists of feedback circuit that measures the amount of light the laser itself is generating, and controls how much current goes to the laser diode to control the brightness output over the life of the laser. In addition, provision is made to strobe the laser for each point to be digitized, rather than continuous operation, resulting in increased positional accuracy.

FIG. 6/6A consists of several circuits to determine and generate the digital signals necessary for the computer to obtain X, Y and Z information for each data point digitized. The first circuit 72 comprises U-1 and parts of U-3 and U-30; its purpose is to take the video signal from the charge coupled photodiode, scan out all of the diode pixels (which may be about 1000) for each point being interrogated, and find which of the pixels has the greatest intensity. This data is used to determine the height (Z-axis) information. The circuit used to determine the pixel with the greatest light intensity consists of a comparator that compares each pixel coming from the charge coupled photodiode to the previous pixel; when it detects that the previous pixel was of a greater value than the current one, the circuit confirms it has found the pixel with the greatest light intensity in the scan. A counter counts each pixel as it is scanned from the photodiode array. This counter value is latched into some electronic latches 76 and 78 which can later be read by the computer to determine the height information.

The latches 76 and 78 obtain the value to latch from the counter made up of U-10 and U-7 which determine which of the pixels on the array is currently being interrogated. When the highest pixel has been found, the output from this counter is latched into the latches 76 and 78 to be read later by the computer.

Other parts of FIG. 6/6A consist of the counters 80 and 82 made up of U8 and U9 and portions of U12 and U7. These counters are for determining X-axis position via the stepper motor and Y-axis position via the rotate motor. The counters for the Y-axis position are reset automatically with the start of scan indicator which was mentioned in reference to FIG. 4 wherein the probe was discussed. As it is impossible to obtain the count values for the height information (Z-axis), the X-axis, and the Y-axis simultaneously, it is necessary to obtain all of these values during part of the phase of each data point being acquired, and to store them during this same period as they are first acquired. At a later time during this same cycle (and before the next cycle starts to gather other data points), all of the X, Y and Z data is brought together in one set of buffers so that it can be read out by the computer all as one data point. Secondary buffers are indicated at 84 comprising U-13, U-14, U-15 and U-16.

Another portion of FIG. 6/6A consists of a group 86 of single shot multivibrators which are comprised of U-5 and U-6. U-5 is used to determine when the laser strobes during the data acquisition cycle, and also the duration of the laser strobe during data acquisition. U6 is used to determine when to generate a start of scan signal to scan the data from the charge-coupled photodiode array.

All of the data for each pixel is represented as a four byte double word—that is the equivalent of 32 bits of information. In these 32 bits is represented X, Y and Z for each pixel. For every point, therefore, 32 bits of information need to be sent to the computer. To minimize the number of connections, it was necessary to multiplex these 32 bits onto 16 lines which go to the computer. Therefore, U14, U15 and U16 are essentially connected together, but the computer can select which group of 16 (of the 32 bits) should be processed. All connections to the circuit of FIG. 6/6A are made through J1, which then goes to the computer interface circuit, FIG. 7. Additionally, lines on connector J-1 consist of control lines necessary to manipulate the probe and the 16 above mentioned data lines. Various control signals are available to turn the laser on and off, to reset the sled, to manually set the sled either forward or backward, to enable the rotate motor to reset all the system counters, and to switch between the low and high 16 bits which comprise the 32 bit words.

Figure 7:
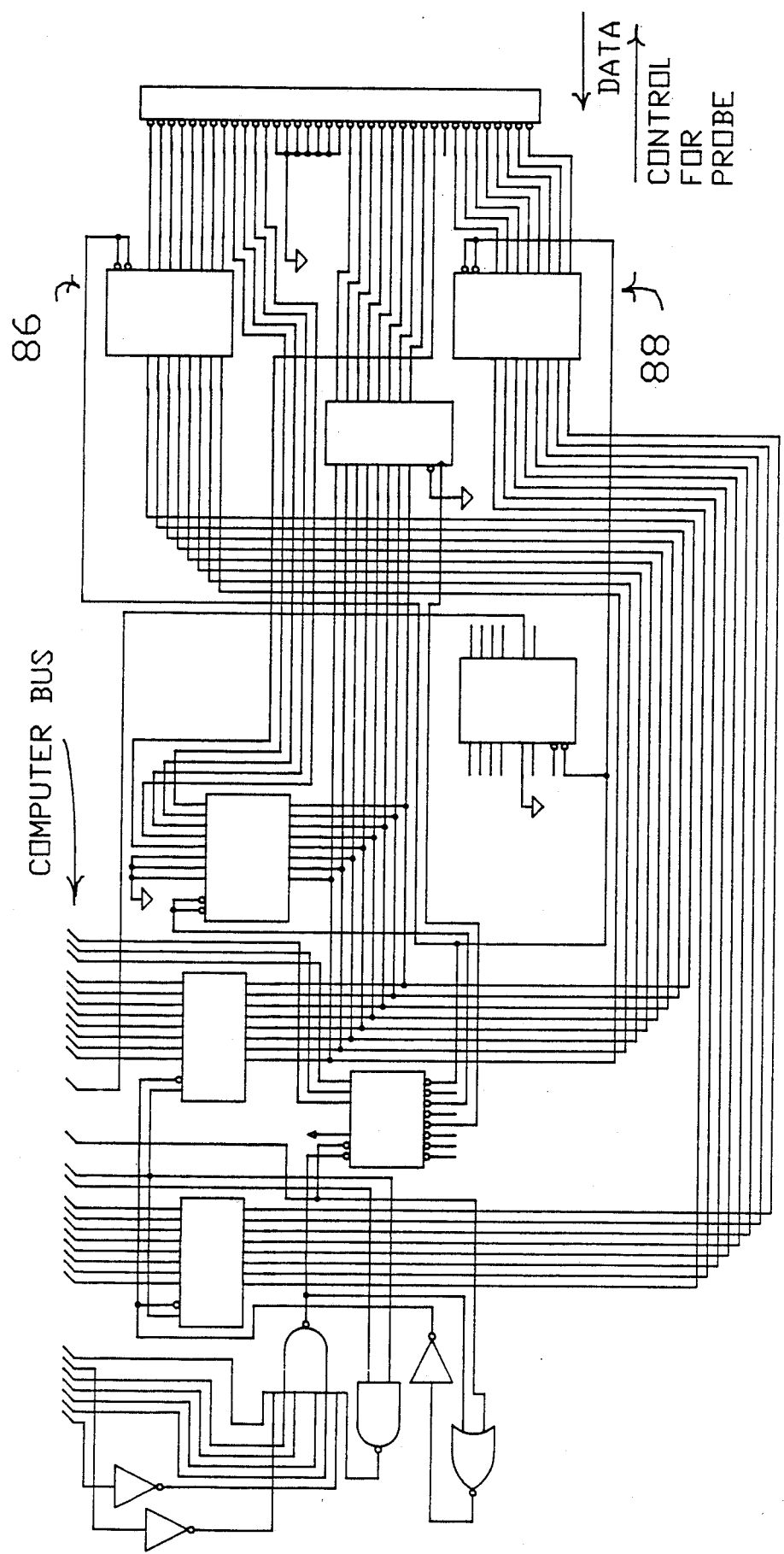

FIG. 7 is a schematic diagram of an electronic circuit board that plugs into an IBM-AT or other compatible computer. This card is used to interface between the computer bus and external electronics necessary to control the probe, comprising the circuits of FIGS. 5/5A and 6/6A. The system comprising latches 86 and 88 to read the data in (U-9 and U-10 in FIG. 7), and some additional bus interface components. The data which is obtained for each point of interest comes in as 32 bits, and is stored in a separate memory in the AT or compatible computer (or other type of computer) which has been installed for this particular purpose. An additional memory card, not shown in the drawings, is used to store the scan data.

One complete scan of the probe scans essentially three teeth which results in a scan area of approximately one centimeters by three centimeters, and the data gathered may consist of 256 separate points in one direction of the tooth and 200 points in the other direction; thus, the amount of memory required to store a complete scan of three teeth is on the order of 750 kilobytes.

Figure 8:
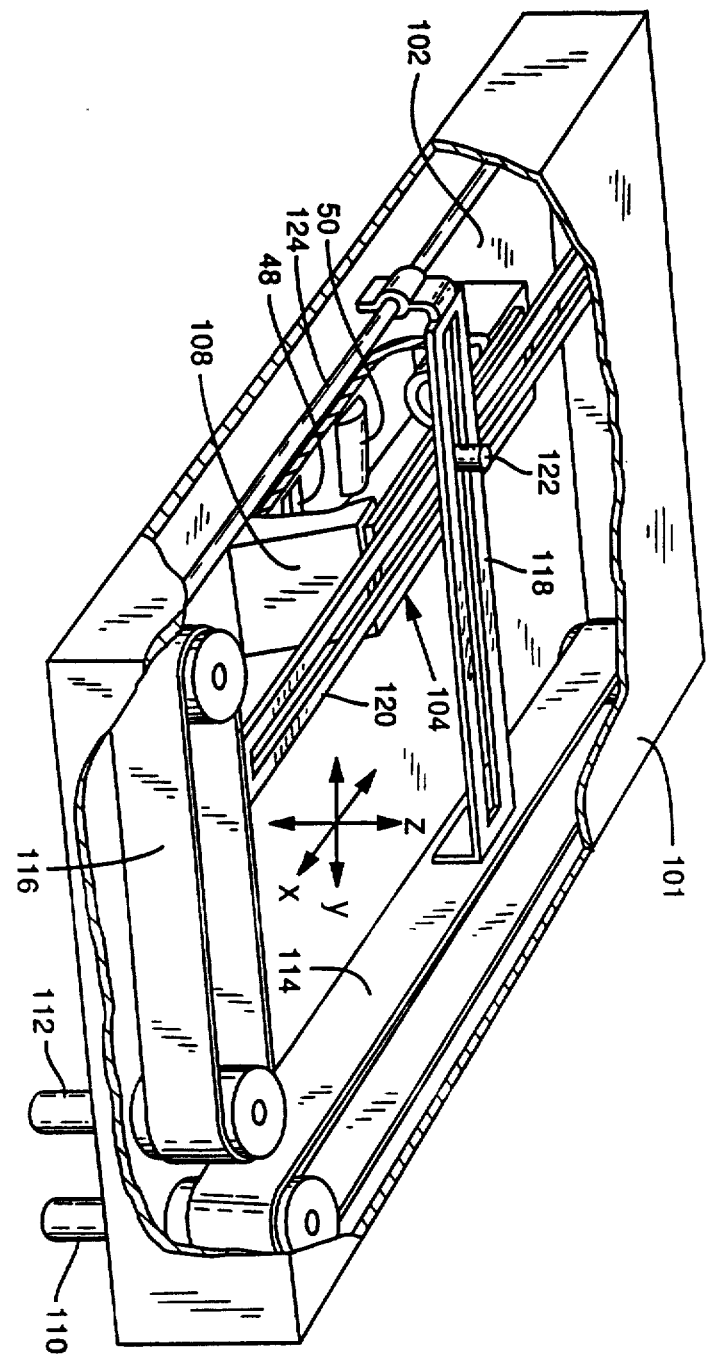
FIG. 8 is a perspective view showing another embodiment of the invention.

FIG. 8 is a somewhat schematic view in perspective, showing a variation of the present invention whereby a wider area or volume can be scanned and mapped in three dimensions, with somewhat less resolution than in the previous embodiment. This system can be used, for example, to map the locations and topographies of all the teeth in a patient's mouth, or at least teeth which are not adjacent to one another. This can give the dentist or laboratory technician the relative positions of the teeth and of the features of the teeth, generally similar to the information obtained from a full-mouth impression of the patient's teeth. This relatively low density full-mouth scan information can be merged in the computer with the high resolution scan information obtained in the other scans for particular teeth. It can be merged by recognition of features (cusps) on the teeth or by fiducials deliberately put on the teeth (e.g. black dots).

FIG. 8 shows a pair of plates 101 and 102, of which this bottom plate 102 is transparent. These plates are held a fixed distance apart in parallel relationship as shown, and a scanner 104 is closely fitted between the plates. The scanner 104 has flat upper and lower surfaces, and the spacing between the plates 101 and 102 is such that the scanner can be moved in all X and Y directions between the plates with little friction. At the same time, the spacing is such that the scanner 104 has virtually no freedom of movement in the up and down or Z direction.

The scanner unit 104 can comprise virtually the same scanner unit or module shown in FIG. 2 inside the housing and near the tip of the probe device—i.e., a part of the platform or sled 28 shown in FIG. 2, with the laser diode 44, the focusing lens 46, and the photodiode array 52, as well as the exit slit 48 and the cylindrical lens 50 for focusing the returning light onto the photodiode array, all in the same triangulation arrangement described above. However, the rotating polygon or other type scanner of the earlier embodiment is replaced with a fixed angled mirror 108. Thus, the modified scanner unit 104 can in itself obtain Z-axis information only. X and Y-axis data are obtained by the known position of the scanner unit 104 at any time. A scanner position monitoring apparatus 110 which is fixed relative to the parallel plates 101 and 102 has position monitors or encoders which generate signals giving the X and Y position of each spot surveyed as the scanner unit is moved around between the plates while scanning the teeth or other topography. The scanner unit 104 may be moved manually around the mouth, or by a manipulating unit 112 which moves the unit through enough positions that sufficiently detailed information regarding the relative positions and features of the teeth can be obtained. For this type of survey, the laser diode should emit a pulse beam, so that dwell at any one point is limited and so that each surveyed point is examined only once. The unit 104 is preferably is moved continuously in the mapping operation. This differs from the previous embodiment, wherein the beam is constantly undergoing a scanning or sweeping in the Y-axis direction due to the movement of the rotating polygon mirror.

The X and Y axes are controlled by a motor/encoder or stepper motors for each axis (not shown) mechanically connected to X drive and Y drive input shafts 110 and 112. The X and Y drive shafts may be driven with pulses which also control the pulsing of the laser, as described above.

The configuration shown in FIG. 8 is one example of an X and Y scan positioning device. In the illustrated construction, taut bands 114 and 116 move X and Y drive actuators 118 and 120 which are connected to the scan unit 104 by a guide peg 122. A guide rail 124 may guide the motion of each of the actuators 118 and 120.

The scanner shown in FIG. 8 can be used for rapid scans at low resolution or for slower scans at corresponding higher resolution. Driving of the X and Y input shafts 110 and 112 can be effected manually, i.e. by button or joystick control or the two motors; or under computer control in accordance with a predefined scan path, or automatically following the pattern of the teeth.

Figure 9:
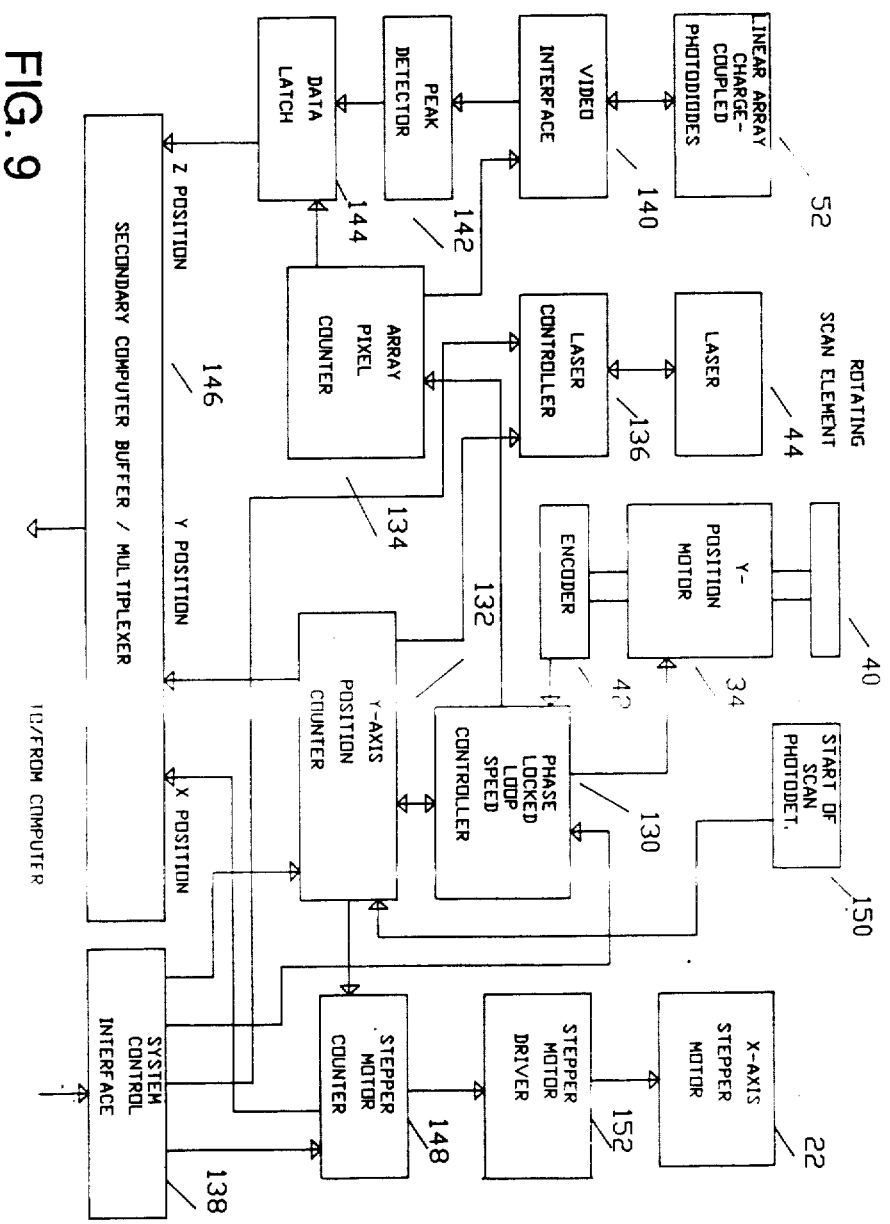
FIG. 9 is a block diagram illustrating some of the operational features of the system of the invention

FIG. 9 is a block diagram of the system of the invention, showing control and information feed lines. Item 40 is the rotating scan element connected by a shaft to the Y position motor 34. Also connected to the Y position motor 34 is an encoder 42. These elements are shown connected to the phase lock loop speed controller 130. An arrow from the controller 130 to the Y position motor indicates direct driving of the motor. The output from the encoder is shown feeding into the phase lock loop speed controller 130 to control the motor speed.

One of the outputs of the phase lock loop controller 130 goes to the Y-axis position counter 132 which keeps track of the position of the scanned beam in the Y direction. Another output from the phase lock loop speed controller connects to the array pixel counter 134, which is used to trigger the photodiode array to start the scan for each new point needed to be interrogated.

To the left of the Y position motor 34 is shown the laser 44, and a connection to its controller 136. The laser controller 136 has two sources of input: one is from the Y-axis position counter 132 which is used to strobe the laser controller, which can then strobe the laser in synchronization with the positioning of the Y-axis; the other input to the laser controller comes from the system control interface shown as the block 138 in the lower right of the drawing. The system control interface is directly controlled by the computer so that the laser beam can be independently turned on and off by the computer.

To the left of the laser on the block diagram is shown the linear array charge coupled photodiode 52. It is shown connected to its photodiode interface 140. The output of the photodiode interface sends its signals to the peak detector 142 to determine which pixel has the greatest intensity, thereby determining Z information. The output of the peak detector 142 goes to the data latch 144 which causes the output from the array pixel counter 134 to be latched into the data latch when the pixel with the most light on it is detected; this is used as the Z position information.

The block labeled 146 shows the secondary computer buffers and multiplexer. The output from the data latch 144, from the Y-axis position counter 132, and from the stepper motor counter 148 are all fed into this multiplexer. This gives the computer all three coordinates it requires in determining X, Y and Z.

To the right of the rotating scan element 40 is a block showing the start of scan photodetector 150. The output of this start of scan photodetector is an input to the Y-axis position counter 132, and is used to reset the counter when the laser beam scans past this photodetector.

The output of the Y-axis position counter 132 also is used to go to the stepper motor counter 148, so that, after every 256 positions of Y-axis, the stepper motor counter is incremented one step in the output of the stepper motor counter. The stepper motor counter drives the stepper motor driver 152, which in turn also drives the actual X-axis stepper motor 22.

In addition, the system control interface block 138 can manually control the stepper motor counter 148 to control the stepper motor under computer control for fast movements such as retract after scanning the teeth.

The above described preferred embodiments are intended to illustrate the principles of the present invention, but not to limit the scope of the invention. Other embodiments and variations to these preferred embodiments will be apparent to those skilled in the art and may be made without departing from the scope of the invention as defined in the following claims.

I claim:

1. A system for three dimensional mapping of the topography of a small object, and for generating digitized signals indicative of the topography, for use in viewing the topography in a three dimensional representation on a screen and/or for generating a model of the topography, comprising, a probe housing for placement adjacent to the small object or objects to be surveyed, slidable sled means mounted in the housing so as to slide in and out longitudinally on the housing in an X-axis direction, first motor means for advancing the sled means along the X-axis direction, first position means associated with the motor means and the sled means, for recording the position of the sled means, to produce X-axis readings at surveyed points, beam scanning means on the sled means, for repeatedly scanning a focused beam of light across the surfaces of the small objects, by swinging the beam from a rotational point of origin, second motor means associated with the beam scanning means, for causing the beam to be scanned, second position means associated with the second motor means, for encoding the position of the beam scan and generating a signal in accordance therewith, for each point surveyed, representing Y-axis positional information, perpendicular to the X axis, and triangulation light sensor means on the sled means, mounted off-axis with respect to the light beam, for detecting the depth of a surveyed point away from the sled means, and third position means for encoding the depth and for generating a signal in accordance therewith, representing Z-axis or depth information, whereby a series of points on the small object are surveyed, with each point assigned X-axis, Y-axis and Z-axis information, so that the topography of the small object can be reproduced with the aid of a computer.

2. The mapping system of claim 1, including means for surveying said points at least as densely as every 50 microns along the small object.

3. The mapping system of claim 1, wherein the beam scanning means includes a laser diode producing a laser beam which is focused and rotationally scanned.

4. The mapping system of claim 3, further including a photodetector positioned in the scanned path of the laser beam, at an appropriate position to indicate a start of scan of each scan of the beam, whereby variations in the actual scan path from the beam scanning means are reduced.

5. The mapping system of claim 1, wherein the first motor means comprises a stepper motor, with said first position means associated with the stepping function.

6. The mapping system of claim 5, wherein the first motor means includes a screw advancing mechanism.

7. The mapping system of claim 1, wherein the triangulation light sensor means comprises a photodetector array, with a cylindrical lens focusing light from the surveyed point onto the photodetector array, the cylindrical lens being arranged to substantially exclude light which would give other than Z-axis information.

8. The mapping system of claim 1, wherein the housing has overall dimensions along the Y and Z axes not exceeding 16 millimeters.

9. The mapping system of claim 8, wherein the housing includes a transparent window through which the beam is projected and detected, and the housing being substantially sealed against moisture and adaptable for insertion in a dental patient's mouth for surveying the topography of teeth.

10. The mapping system of claim 1, wherein the platform means is mounted in the housing with spring-loaded roller bearings, so that variation in the path of movement is avoided, for insuring accurate readings.

11. The mapping system of claim 1, including a laser diode as a source of the light beam, the laser diode having means for producing a pulsed beam which is synchronized with the timing of surveying of points on the small object being mapped.

12. The mapping system of claim 1, wherein the triangulation light sensor means comprises a photodetector array.

13. A method for mapping in three dimensions the topography of a dental patient's tooth, comprising, providing a probe of narrow dimensions having a housing capable of being inserted comfortably into the patient's mouth, advancing a platform or sled within the housing longitudinally with respect to the housing along an X axis, while recording the position of the sled representative of X-axis position of points surveyed, while the platform is advancing along the X axis, scanning a laser beam to sweep across a tooth, and encoding the position of the beam in its sweep and generating a second signal representative of a Y-axis position of the beam and thus of each point being surveyed, while the beam is being scanned across the tooth, sensing the position at which the beam impinges on the tooth with an off-axis photodetector means spaced away from and off the axis of the beam on the platform, so as to determine the height of each surveyed point from the platform by triangulation via the laser beam and the detector position, and encoding the detected position and generating a signal in accordance therewith, for Z-axis information, receiving all of the signals for X-axis, Y-axis and Z-axis information in a computer and generating with the computer from said signals an image of the topography of the tooth in three dimensions, usable for displaying an image for review and editing of or for generating a model of the tooth's topography with a model producing apparatus.

14. The method of claim 13, wherein the laser beam is scanned substantially from a point on the platform or sled, by a rotating scan element, so that the beam sweeps in an arcuate path across the tooth, and further including pre-calibrating the probe to compensate for the arcuate scan path, by scanning a surface having known distance points from the probe sled and recording incremental error distances and storing them in computer memory and using them to correct height measurements taken by the probe.

15. The method of claim 14, wherein the surface used for calibration scanning is an inclined plane arranged symmetrically about the X axis.

16. A three dimensional scanner device for obtaining and recording three dimensional information concerning the topography of an object, comprising, triangulation means for determining one dimension of the object, a height dimension, said triangulation means including a light beam source producing a beam, and detection means for receiving light from surfaces of the object off-axis from the beam to determine height by triangulation, width scanner means for scanning the beam through a scan path in a width direction, width position determining means for recording a width position for each point recorded by the triangulation means, based on the position of the scanner means at each subject point, and depth scanner means for moving the width scanner means and the triangulation means along a depth axis, and depth position determining means for determining and recording a depth position along the depth axis, for each point recorded by the triangulation means, based on position of the scanner means along said depth axis.

17. The three dimensional scanner of claim 16, in an outer housing having dimensions not exceeding about 16 mm in width.

18. The three dimensional scanner of claim 16, wherein the detection means comprises an array of photodetectors.

19. The three dimensional scanner of claim 16, wherein the light beam source comprises a laser diode, and the scanner means includes a rotating multi-faceted polygon mirror in the path of the beam and positioned to sweep the beam across the surfaces of the object.

20. The three dimensional scanner of claim 16, wherein the light beam source comprises a laser diode, and the scanner means includes a holographic scanner.

21. The three dimensional scanner of claim 16, wherein the triangulation means comprises a height scanner unit having the beam source and the detection means, and including a pair of parallel plates between which the height scanner unit is closely positioned and slideable, one of the plates being light-transmissive, and wherein the width and depth scanner means comprise X and Y manipulation means for moving the height scanner unit on X and Y axes, independently or simultaneously.

* * * * *

UNITED STATES PATENT AND TRADEMARK OFFICE
CERTIFICATE OF CORRECTION

PATENT NO. : 4,935,635
DATED : June 19, 1990
INVENTOR(S) : Dale G. O'Harra It is certified that error appears in the above-identified patent and that said Letters Patent is hereby corrected as shown below:

The sheets of Drawing consisting of Figures 8 and 9 should be added as per attached sheets.

Signed and Sealed this

Thirty-first Day of March, 1992

Attest:

HARRY F. MANBECK, JR.

*Attesting Officer*      *Commissioner of Patents and Trademarks*